United States Patent
Bergqvist et al.

(10) Patent No.: US 11,001,510 B2
(45) Date of Patent: May 11, 2021

(54) LIQUID TREATMENT SYSTEM

(71) Applicant: Wallenius Water Innovation AB, Stockholm (SE)

(72) Inventors: Johan Bergqvist, Saltsjo-Boo (SE); Staffan Strand, Stockholm (SE); David Skantze, Saltsjo-Boo (SE)

(73) Assignee: Wallenius Water Innovation AB, Stockholm (SE)

( * ) Notice: Subject to any disclaimer, the term of this patent is extended or adjusted under 35 U.S.C. 154(b) by 0 days.

(21) Appl. No.: 16/485,997

(22) PCT Filed: Feb. 16, 2018

(86) PCT No.: PCT/SE2018/050150
§ 371 (c)(1),
(2) Date: Aug. 14, 2019

(87) PCT Pub. No.: WO2018/151659
PCT Pub. Date: Aug. 23, 2018

(65) Prior Publication Data
US 2020/0231470 A1   Jul. 23, 2020

(30) Foreign Application Priority Data
Feb. 17, 2017   (SE) .................................... 1750158-6

(51) Int. Cl.
*C02F 1/32* (2006.01)
*B08B 1/00* (2006.01)

(52) U.S. Cl.
CPC .............. *C02F 1/325* (2013.01); *B08B 1/001* (2013.01); *C02F 2201/324* (2013.01); *C02F 2201/3223* (2013.01)

(58) Field of Classification Search
CPC .............. C02F 1/325; C02F 2201/3223; C02F 2201/324; B08B 1/001; B08B 1/005
See application file for complete search history.

(56) References Cited

U.S. PATENT DOCUMENTS

| | | | |
|---|---|---|---|
| 3,904,363 A | * | 9/1975 | Free ........................ C02F 1/325 250/431 |
| 4,017,734 A | | 4/1977 | Ross |

(Continued)

FOREIGN PATENT DOCUMENTS

| | | |
|---|---|---|
| EP | 785907 B1 | 8/1999 |
| EP | 1371611 A1 | 12/2003 |

(Continued)

OTHER PUBLICATIONS

Swedish Search Report for Swedish Patent Application No. 1750158-6 dated Sep. 15, 2017.

(Continued)

*Primary Examiner* — Eliza W Ozenbaugh-Stewart
(74) *Attorney, Agent, or Firm* — Harness, Dickey & Pierce, P.L.C.

(57) ABSTRACT

A liquid treatment system comprising at least one ultraviolet light treatment lamp arranged within an elongated protective UV-transparent sleeve provided along a central longitudinal axis A, said sleeve having an outer surface and an essentially circular cross-sectional shape; and an elongated reactor configured to receive said sleeve, whereby an elongated liquid treatment chamber for receiving liquid to be treated, is provided between an inner surface of the reactor and the outer surface of the sleeve; wherein said liquid treatment system further comprises at least one cleaning arrangement comprising at least one cleaning device, wherein said cleaning arrangement is configured to compress said cleaning device towards the outer surface of the sleeve and to transfer the cleaning device over the sleeve surface for cleaning the outer surface of the sleeve, wherein the at least one cleaning device comprises at least one metal braid.

15 Claims, 8 Drawing Sheets

(56) References Cited

U.S. PATENT DOCUMENTS

| | | | |
|---|---|---|---|
| 5,227,140 A | 7/1993 | Hager et al. | |
| 5,266,280 A * | 11/1993 | Hallett | B01J 19/123 |
| | | | 422/186 |
| 5,782,270 A * | 7/1998 | Goett | H01R 9/0521 |
| | | | 138/109 |
| 5,937,266 A | 8/1999 | Kadoya | |
| 6,590,217 B1 * | 7/2003 | Freeman | A61L 2/10 |
| | | | 250/435 |
| 7,159,264 B2 | 1/2007 | Sotirakos et al. | |
| RE39,522 E | 3/2007 | Ishiyama | |
| 2001/0032659 A1 | 10/2001 | Wang et al. | |
| 2001/0047811 A1 * | 12/2001 | Sivacoe | B08B 9/0553 |
| | | | 134/8 |
| 2004/0036033 A1 * | 2/2004 | Snowball | C02F 1/325 |
| | | | 250/431 |
| 2004/0099406 A1 * | 5/2004 | Schildmann | B08B 9/055 |
| | | | 165/95 |
| 2004/0262236 A1 | 12/2004 | Hoffmeier | |
| 2006/0123571 A1 | 6/2006 | Sotirakos et al. | |

FOREIGN PATENT DOCUMENTS

| | | |
|---|---|---|
| EP | 1714944 A1 | 10/2006 |
| GB | 710903 A | 6/1954 |
| GB | 2389577 A | 12/2003 |
| GB | 2529041 A | 2/2016 |
| KR | 20100044762 A | 4/2010 |
| WO | WO-2016/020693 A1 | 2/2016 |

OTHER PUBLICATIONS

International Search Report PCT/ISA/210 for International Application No. PCT/SE2018/050150 dated Apr. 20, 2018.

* cited by examiner

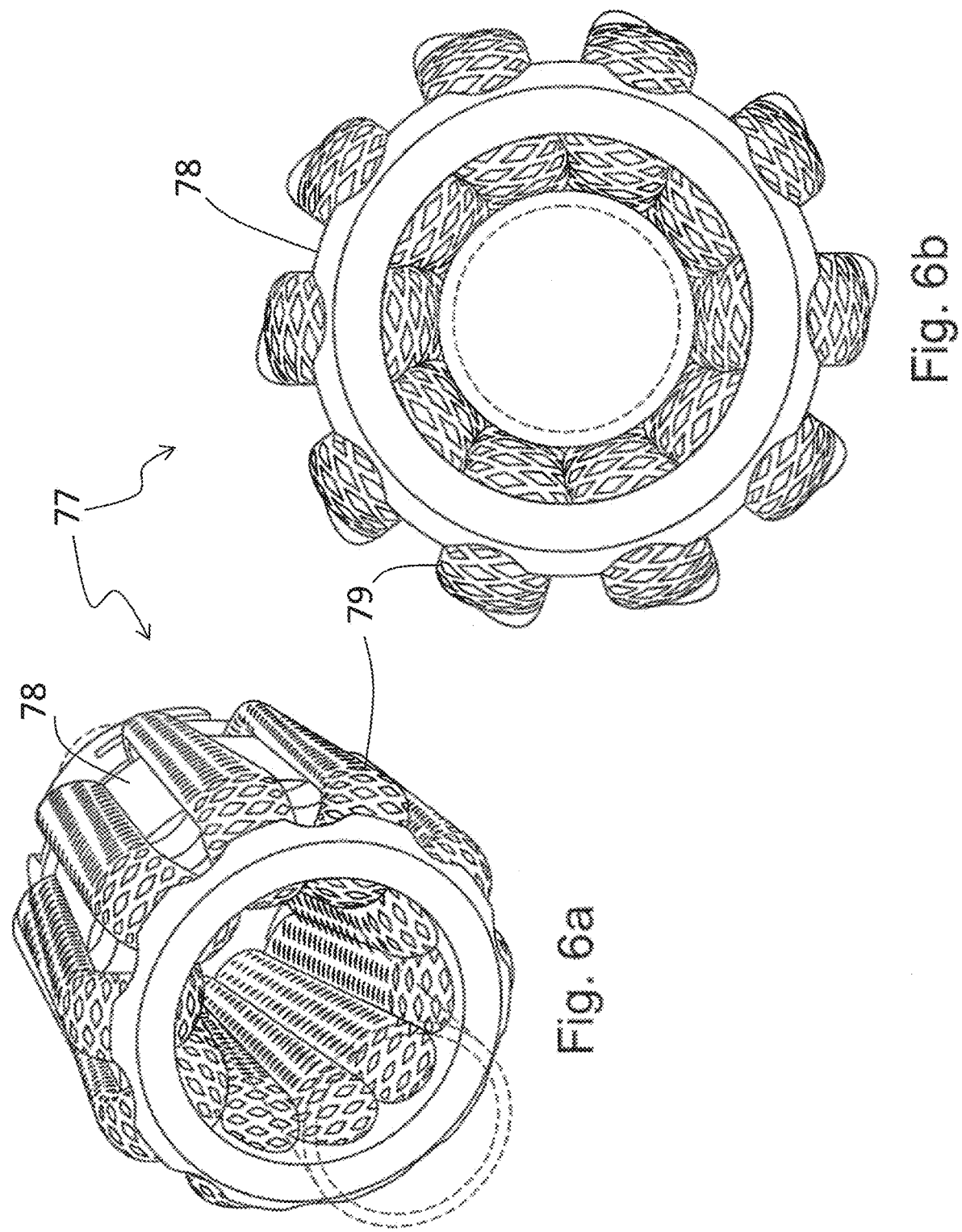

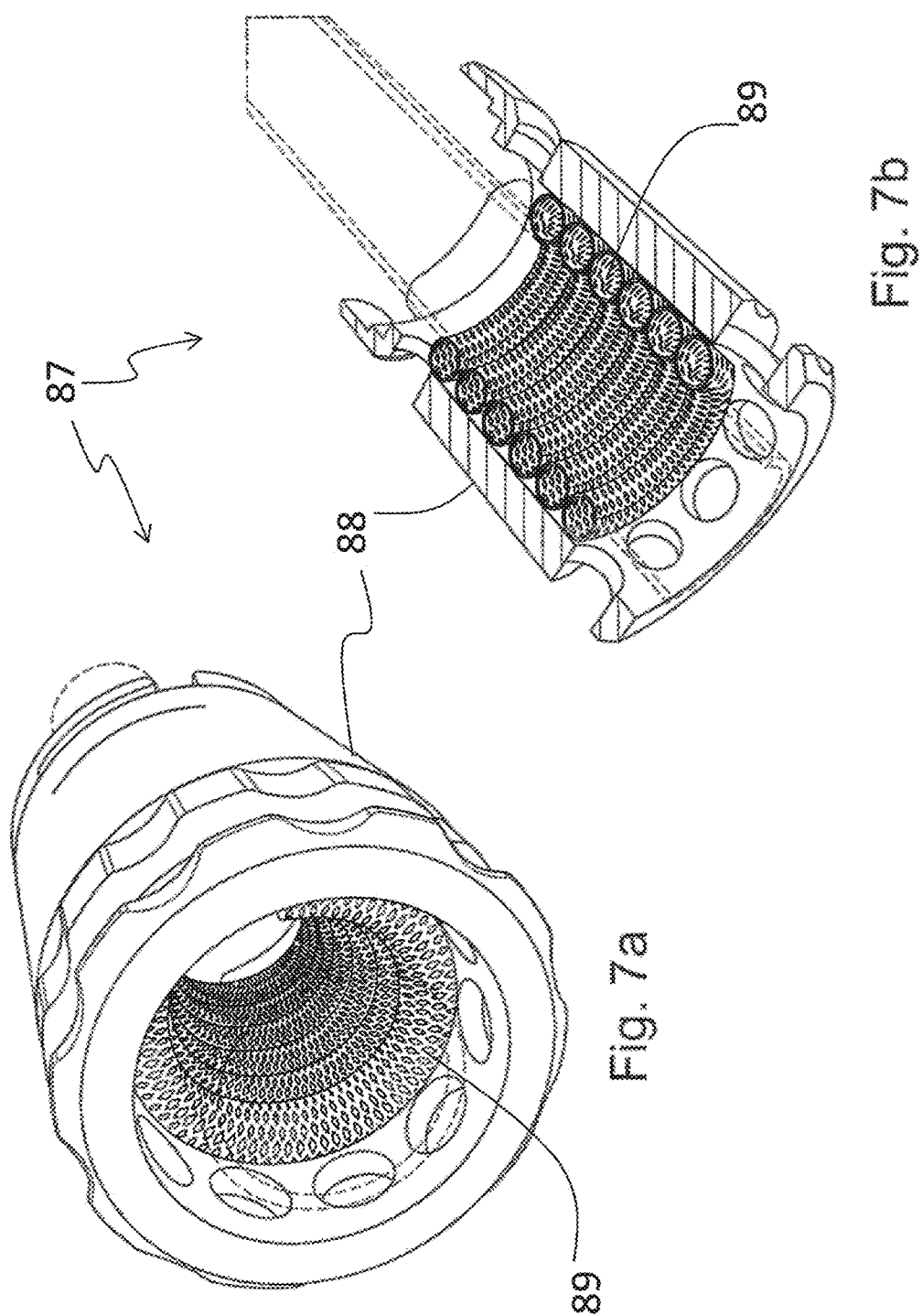

LIQUID TREATMENT SYSTEM

CROSS-REFERENCE TO RELATED APPLICATIONS

This application is a national phase under 35 U.S.C. § 371 of PCT International Application No. PCT/SE2018/050150 which has an International filing date of Feb. 16, 2018, which claims priority to Swedish Application No. 1750158-6, filed Feb. 17, 2017, the entire contents of each of which are hereby incorporated by reference.

TECHNICAL FIELD OF THE INVENTION

The present invention relates to a liquid treatment system comprising at least one ultra-violet (UV) light treatment lamp and comprising at least one cleaning arrangement.

RELATED ART

There are many applications where UV light sources are used for treating liquids. Wallenius Water AB in Sweden has developed and is selling liquid treatment equipment comprising an elongated tubular treatment chamber with an inlet and an outlet. In the treatment chamber at least one generally tubular protective UV transparent sleeve (e.g. made from fused quartz) is arranged and inside the sleeve is a UV light source arranged, such as a lamp capable of generating wavelengths in the UV region.

Another type of treatment reactor developed by the applicant also comprises a treatment chamber having oppositely arranged in- and outlets, where the UV light sources are arranged in elongated sleeves, e.g. fused quartz sleeves. These sleeves are arranged perpendicular to the flow of liquid to be treated through the treatment chamber.

The above described treatment units are functioning very well for treating all sorts of liquids for example water, where the latter described treatment unit is specially adapted for treatment of ballast water in ships. The liquid that is treated often comprises particles and other solid matter other than the organisms that are killed off by the treatment units. These particles, as well as other residue from the killed off organisms, have a tendency to stick on the interior surfaces of treatment units. These particles, and other residue, aggregated on the surface are generally denoted as fouling.

UV light treatment, more specifically UV-light in combination with heat, sometimes provokes chemical reactions resulting in depositions on the interior surfaces. These resulting depositions are generally denoted as scaling.

Often scaling is more difficult to remove from the surface than fouling.

This means that in order to have an optimum efficiency of the treatment device the interior has to be cleaned regularly. According to one solution in the prior art cleaning is performed by injecting cleaning liquids into the treatment chamber, where the cleaning liquids are developed for removing the fouling or scaling on the surfaces. However, even if they are efficient for removing fouling/scaling and the like deposits on the surfaces of the treatment chambers, they require that the treatment units are closed down during a period of time, whereby thus no treatment of liquid may be performed.

According to other suggestions, various forms of wiper mechanisms have been designed to remove fouling/scaling from surfaces. All such forms of wiper mechanisms act to "wipe off" the layer from the external surface of the sleeve. Such wiper mechanisms often require a large annular space between the outside surface of the sleeve housing the UV lamp and the surrounding tubing housing the sleeve in order to accommodate the wiper mechanism. The treatment system relies on the transmittance of the liquid in order to allow the UV photons to reach the contaminants in the liquid passing through the annular region between the sleeve and housing.

Some patents and patent applications within the technical field will now be briefly discussed in the following.

EP1371611 relates to a fluid treatment apparatus. A cleaning assembly comprising a plurality of cleaning heads is provided. The cleaning heads each comprise a plurality of portions of titanium dioxide which are biased against the surface of the respective UV lamps.

U.S. Pat. No. 5,227,140 relates to a modular self-cleaning oxidation chamber comprising a shuttling scraper including an annular wiper that simultaneously cleans the inside surface of the surrounding tubular module as well as the outside surface of an enclosed quartz tube. The wiper is driven by the liquid and has the form of an annular disk and being composed of a fluoroelastomer.

EP1714944 relates to a fluid disinfection apparatus of a kind similar to the apparatus of EP1371611. A cleaning material may be a fabric or metal, e.g. a metal gauze covered by titanium dioxide and may be biased into contact with the ultra-violet light source.

U.S. Pat. No. 7,159,264 discloses a scraper for cleaning tubular members. The scraper comprises a plurality of concatenated resilient segments adapted to contact the exterior surface the tubular member. The resilient member is made up from a resilient wire. The cleaning effect of the tubular member is achieved when the scraper is moved axially with regard to the tubular member.

USRE39522 relates to ultraviolet ray irradiation equipment having scraper rings fitted to light transmission tubes. The scraper ring defines a cleaning solution chamber to be in contact with the outer surface of a tube. The scraper may be made from a non-elastic material such as Teflon® and stainless steel. The frequency of cleaning is determined upon the quantity of scale and is exemplified as two to three times a day.

U.S. Pat. No. 5,937,266 relates to a light irradiating device equipped with a cleaning mechanism. The mechanism comprises scrapers adapted to slide along the outside surface of the light-transmitting tubes. The material used for the scraper may rubber or Teflon®, or a cleaning cloth.

EP0785907 relates to a shuttling scraper including a wiper cartridge, configured to clean the outside surface of a quartz tube. The cartridge may be filled with a scrubber material which may consist of stainless steel turnings or stainless steel wool. When the shuttling scraper is in a parked position the wiper cartridge is protected from UV radiation and the heat of the UV lamp, which also helps to extend the life of the wiper cartridge.

The above prior art documents disclose various UV-light treatment apparatuses that include mechanical cleaning members provided with various materials for removing fouling/scaling from a UV-lamp surface.

Despite the various solutions suggested in the above prior art some drawbacks still remain in particular with regard to remove harder material, i.e. scaling, from the outer surface of the UV-transparent sleeve enclosing the UV-lamp.

SUMMARY

It is an object of the invention to provide an improved liquid treatment system provided with means capable of efficiently removing harder material from the outer surface of the sleeve. This is achieved in a liquid treatment system according to claim 1.

In one aspect of the invention a liquid treatment system is provided comprising:

- at least one ultra-violet (UV) light treatment lamp arranged within an elongated protective UV-transparent sleeve provided along a central longitudinal axis A, said sleeve having an outer surface and an essentially circular cross-sectional shape; and
- an elongated reactor configured to receive said sleeve, whereby an elongated liquid treatment chamber for receiving liquid to be treated, is provided between an inner surface of the reactor and the outer surface of the sleeve; wherein said liquid treatment system further comprises
- at least one cleaning arrangement comprising at least one cleaning device, wherein said cleaning arrangement is configured to compress said cleaning device towards the outer surface of the sleeve and to transfer the cleaning device over the sleeve surface for cleaning the outer surface of the sleeve, wherein the at least one cleaning device comprises at least one metal braid.

Hereby an effective cleaning of the sleeve surface can be achieved. The features of the metal braid, such as it shape, elasticity and the metal surface being abrasive will provide good cleaning performance.

In one embodiment of the invention the metal braid is a tubular, hollow cylinder which is braided, knitted or woven from a metallic material. Suitably the metal braid is abrasive and in one embodiment the metallic material is resistant to UV light and corrosion. In one embodiment of the invention the metallic material is stainless steel, monel or titanium.

In one embodiment of the invention the metal braid comprises an elastic inner tube.

In one embodiment of the invention the at least one cleaning device is an elongated cleaning device provided side by side with the sleeve within the liquid treatment chamber and along at least a part of the length of the elongated sleeve, and wherein the cleaning device is compressed towards the outer surface of the sleeve by the cleaning arrangement, wherein the cleaning arrangement is a part of the reactor and wherein at least one of the sleeve and the reactor is configured to rotate around the longitudinal axis A such that the at least one cleaning device will be touching and cleaning the outer surface of the sleeve over essentially the whole circumference of the sleeve.

In one embodiment of the invention the reactor has a partly circular cross-sectional shape with at least one part having an extended radius where the at least one cleaning device is provided and wherein said at least one cleaning device is compressed towards the outer surface of the sleeve by the reactor.

In one embodiment of the invention the at least one cleaning arrangement comprises at least one cleaning unit configured to be moved by a driving arrangement which is structured to drive the cleaning unit in said treatment chamber along said sleeve, the cleaning unit being configured for holding the metal braid of the cleaning device such that the metal braid is compressed towards the outer surface of the sleeve. In one embodiment of the invention the cleaning device encircles the sleeve at least one turn and said cleaning device being resiliently biased to said outer surface of the sleeve by the cleaning unit. In one embodiment of the invention the cleaning unit has a general shape of a tubular body having an inner circular cross-sectional shape adapted to the outer diameter of said sleeve and wherein said cleaning unit has a length extending over only a part of the length of the sleeve.

BRIEF DESCRIPTION OF THE DRAWINGS

FIGS. 6a-6b show schematically three different views of a cleaning arrangement which can be used in a liquid treatment system according to one embodiment of the invention.

FIGS. 7a-7b show schematically two different views of a cleaning arrangement which can be used in a liquid treatment system according to one embodiment of the invention in.

DETAILED DESCRIPTION OF THE INVENTION

Figure 1B:
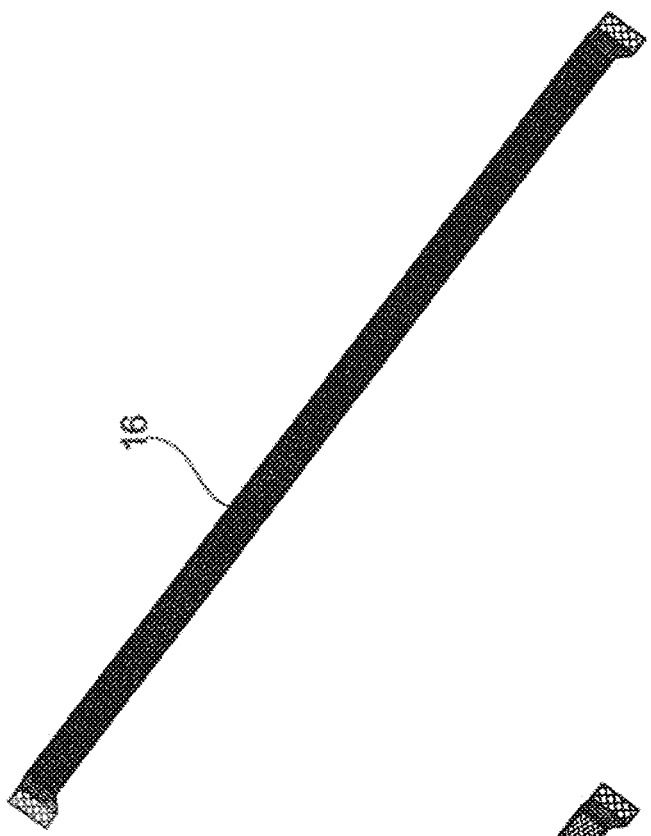
FIG. 1b shows a cleaning device according to another embodiment of the invention.

The invention relates to a liquid treatment system. FIGS. 2-8 show different embodiments of liquid treatment systems 2; 2'; 102; 202; 302 according to the invention. Some of the details are the same or similar in all the embodiments and these details will be given the same or similar reference numbers. In the following description reference is made to all of the FIGS. 1-8. A liquid treatment system according to the invention comprises at least one ultra-violet (UV) light treatment lamp 6 arranged within an elongated protective UV-transparent sleeve 8; 8' provided along a central longitudinal axis A. Said sleeve 8; 8' has an outer surface 10; 10' and an essentially circular cross-sectional shape. The liquid treatment system 2; 2'; 102; 202; 302 comprises further an elongated reactor 12; 12'; 12" configured to receive said sleeve 8; 8'. Hereby an elongated liquid treatment chamber 4; 4' for receiving liquid to be treated, is provided between an inner surface 14; 14' of the reactor 12; 12'; 12" and the outer surface 10; 10' of the sleeve 8; 8'.

According to the invention the liquid treatment system further comprises at least one cleaning arrangement 17; 17'; 77; 87 comprising at least one cleaning device 16; 16'; 79; 89, wherein said cleaning arrangement 17; 77; 87 is configured to compress said cleaning device 16; 16'; 79; 89 towards the outer surface 10; 10' of the sleeve 8; 8' and to transfer the cleaning device 16; 16'; 79; 89 over the sleeve surface for cleaning the outer surface 10; 10' of the sleeve 8; 8', wherein the at least one cleaning device 16; 16'; 79; 89 comprises at least one metal braid. In this patent application and in the claims the term metal braid is meant to cover tubular structures which are braided, knitted or woven from a metallic material such as for example stainless steel, monel or titanium. The metal braid can optionally comprise an inner elastic tube. Metal braids are further described below with reference to FIGS. 1a and 1b.

Figure 1A:
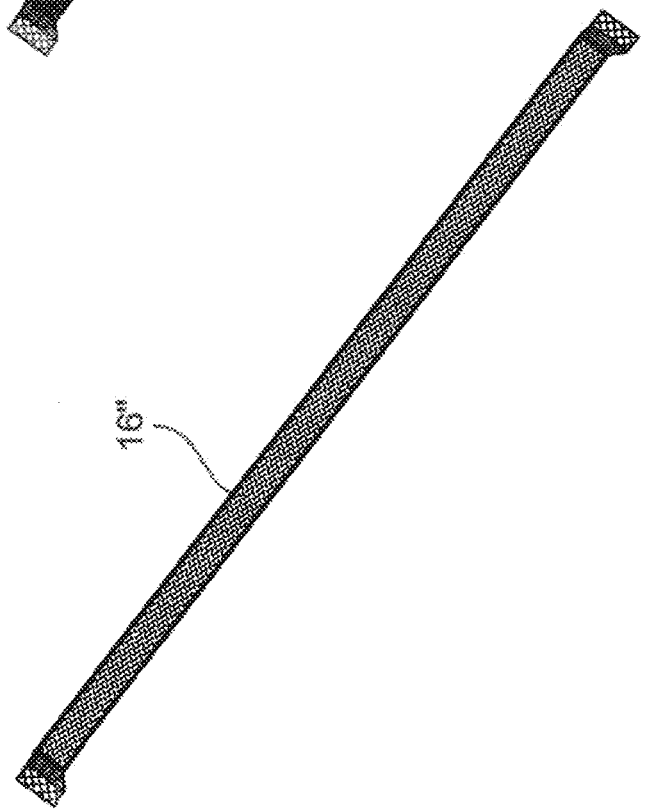
FIG. 1a shows a cleaning device according to one embodiment of the invention.

FIG. 1a shows one embodiment of such a metal braid which can be used in the cleaning device 16; 16'; 79; 89 in any one of the embodiments shown in the FIGS. 2-8. The metal braid is a hollow cylinder, a tube, which is braided, knitted or woven from a metallic material. Furthermore the metal braid is abrasive and the metallic material is suitably resistant to UV light and corrosion. One example of metallic material which can be used for the metal braid is stainless steel. Other examples are Monel and Titanium. In one embodiment of the invention the metal braid is elastic in itself. The metal braid has in one embodiment of the invention an essentially circular cross section. A diameter of the cross section can vary but in one embodiment of the invention the diameter is within 5-30 mm.

Figure 2A:
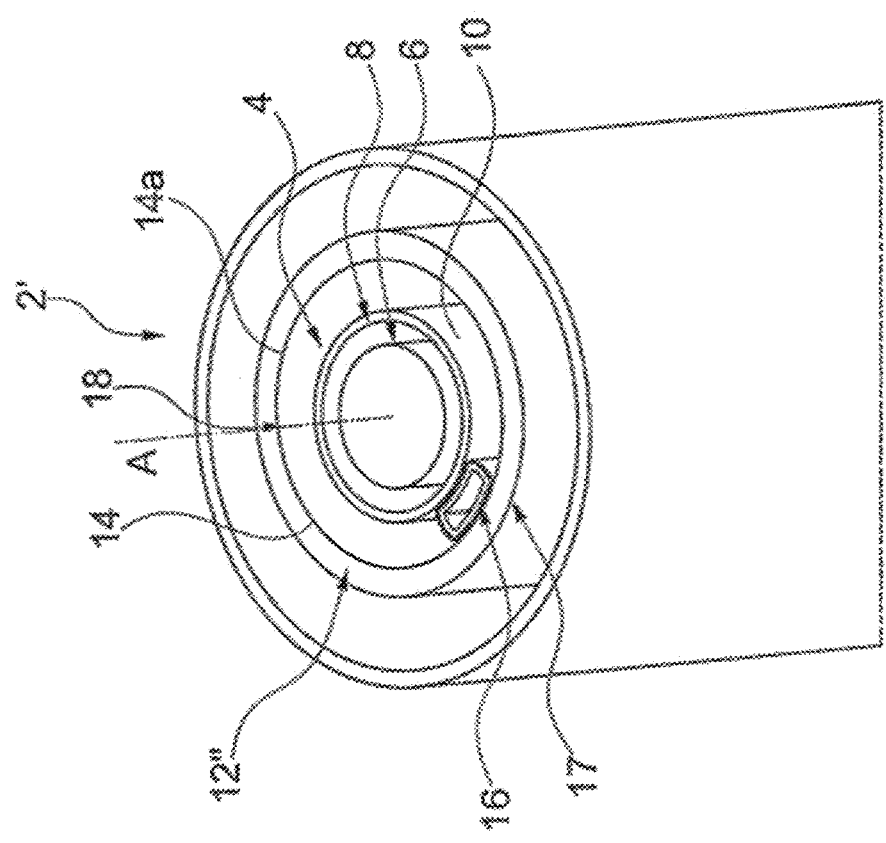
FIGS. 2a-2c show schematically transversal cross sections of three different embodiments of a liquid treatment system according to the invention.

Another example of a cleaning device 16; 79; 89 to be used in systems according to the invention is shown in FIG. 1b. In this embodiment an elastic tube is provided inside the metal braid. The elastic, inner tube provides elasticity to the cleaning device 16; 79; 89 which is important for the cleaning efficiency. Furthermore liquid flow through the cleaning device can be avoided by providing an inner tube. Liquid flow through the metal braid decrease performance of the reactor. Both systems shown in FIGS. 2a and 2b are shown with a cleaning device 16 comprising a metal braid with an elastic tube inside as the one shown in FIG. 1b. However a metal braid without inner tube as described in relation to FIG. 1a can be used in all the embodiments described in this patent application, possibly together with another elastic part.

Figure 2C:
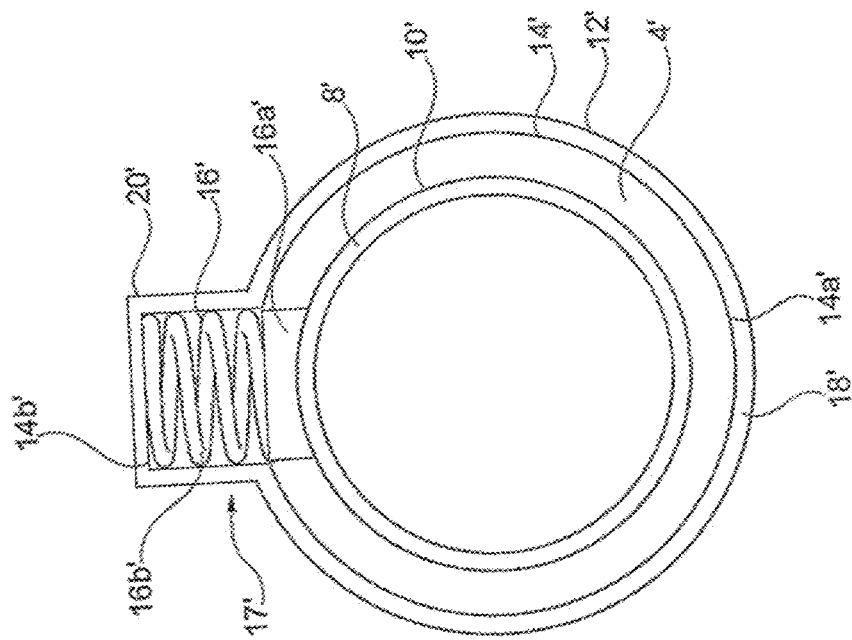
Figure 2B:
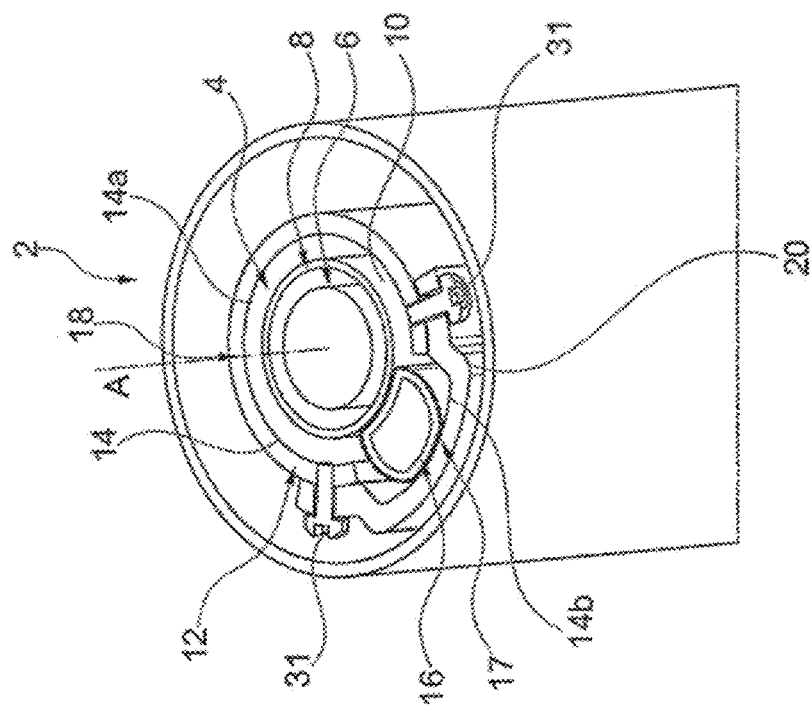
Figure 3:
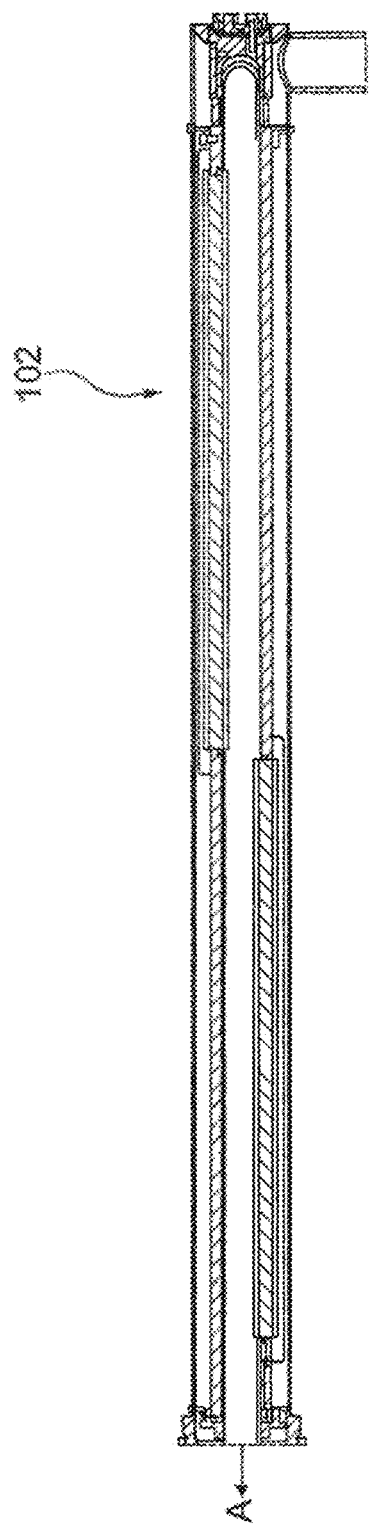
FIG. 3 is a longitudinal cross section of a liquid treatment system according to one embodiment of the invention.

According to some embodiments of the invention, as shown in FIGS. 2-5, said cleaning device 16; 16' is an elongated cleaning device 16; 16' provided side by side with the sleeve 8; 8' within the liquid treatment chamber 4; 4' and along at least a part of the length of the elongated sleeve 8; 8'. In one embodiment of the invention one single elongated cleaning device 16; 16' is provided along essentially the whole length of the sleeve 8; 8'. However in another embodiment of the invention two cleaning devices 16; 16' are provided, one for one part of the length of the elongated sleeve 8; 8', and the other for the rest of the length of the elongated sleeve, whereby the two cleaning devices 16; 16' are provided diametrically opposite each other within the reactor 12; 12'; 12", one on each side of the sleeve 8; 8'. This is shown in FIG. 3 and one reason for providing two cleaning devices 16; 16' instead of one and diametrically opposite each other is because hereby the stress on the sleeve will be decreased. Either each one of the two cleaning devices 16; 16' can be provided along the whole length of the sleeve but diametrically opposite each other or alternatively as described above one cleaning device 16; 16' can be provided for one part of the sleeve and the other for the rest of the sleeve.

Furthermore according to the embodiment of the invention which is shown in FIGS. 2-5 said at least one cleaning device is compressed towards the outer surface 10; 10' of the sleeve 8; 8' by the reactor 12; 12'; 12". This is best shown in FIGS. 2a-2c. in this embodiment at least one of the sleeve and the reactor is configured to rotate around the longitudinal axis A. Either the sleeve 8; 8' or the elongated reactor 12; 12'; 12" is rotated and they can rotate either in one direction or back and forth around the longitudinal axis A such that the at least one cleaning device 16; 16' will be touching and cleaning the outer surface 10; 10' of the sleeve 8; 8' over the whole circumference of the sleeve 8; 8'.

In some embodiments the cleaning device 16; 16' needs to be fastened to the reactor 12; 12'; 12" in some suitable way (not shown). For example the cleaning device 16; 16' can be clamped to the reactor 12; 12'; 12" wall in one or both ends of the liquid treatment system. Other methods for fastening the cleaning device to the reactor can be gluing or screwing at one or more positions along the length of the cleaning device 16; 16'.

FIG. 2a shows a liquid treatment system 2' according to one embodiment of the invention where the reactor 12" is cylindrical and centered around the axis A. The cleaning device 16 is compressed towards the sleeve outer surface 10 by the reactor 12". In this embodiment the cleaning device 16 needs to be secured to the reactor 12" in a suitable way as described above. Hereby the cleaning device 16 will be transferred over the sleeve outer surface 10 when either the sleeve 8 or the reactor 12" is rotated and the sleeve outer surface will be cleaned by the cleaning device 16.

When treating non opaque fluids the distance between the reactor inner wall 14 and the sleeve outer surface 10 is not critical and need not be kept small. In the embodiment shown in FIG. 2a this distance can be made larger. If the distance between the inner wall of the reactor and the outer wall of the sleeve is larger than the uncompressed cleaning device 16 diameter a cleaning device holder could be provided connected to the inner wall 14 of the reactor 12" which cleaning device holder is configured for holding the elongated cleaning device 16 along the sleeve 8 and towards the sleeve outer surface 10. Hereby the cleaning device 16 will be transferred over the sleeve outer surface when either the reactor 12" or the sleeve 8 is rotating around the longitudinal axis A.

Keeping a distance between an outer surface of the sleeve 10; 10' and an inner surface of the reactor 14; 14' small is beneficial when treating opaque liquids. In order to keep this distance small and still provide enough space for a cleaning device the reactor 12; 12' in both the embodiment shown in FIG. 2b and the embodiment shown in FIG. 2c has a partly circular cross-sectional shape with at least one part having an extended radius where the at least one cleaning device 16; 16' is provided.

Describing the design and position of the reactor in the embodiments of FIGS. 2b and 2c, the reactor 12; 12' can be said to be concentric with the sleeve 10; 10' when ignoring the at least one part having an extended radius, i.e. the part or parts of the reactor not having an extended radius has a cross sectional shape being a part of a circle which circle is centred around the central longitudinal axis A.

In some embodiment of the invention (as best shown in FIGS. 2b and 2c) the reactor 12; 12' comprises for each cleaning device 16; 16' a first part 18; 18' having a cross sectional shape being essentially a part of a circle which circle is centered around the longitudinal axis A and a second part 20; 20' connected to the first part 18; 18' and configured for holding the cleaning device 16; 16'. An inner surface 14a; 14a' of the first part 18; 18' and an inner surface 14b; 14b' of the second part 20; 20' together encircle the outer surface 10; 10' of the sleeve 8; 8'. The inner surface 14b; 14b' of the second part 20; 20' being provided at a greater distance from the outer surface 10; 10' of the sleeve 8; 8' than the inner surface 14a; 14a' of the first part 18; 18' is. The second part 20; 20' is hereby the part of the reactor 12; 12' having an extended radius as referred to above. The second part 20; 20' in combination with the cleaning device 16; 16' can also be referred to as a cleaning arrangement 17; 17'. If two cleaning devices 16; 16' are provided, one for one part of the sleeve length and another for another part of the sleeve length as shown in FIG. 3 one first part 18; 18' and one second part 20; 20' will be provided separately for each cleaning device 16; 16'. If on the other hand two cleaning devices 16; 16' are provided each for the whole length of the sleeve but opposite each other the reactor 12; 12'; 12" has to be designed a bit differently than what is shown in FIGS. 2b and 2c. Two second parts 20; 20' may be provided for housing the two cleaning devices.

The distance between the outer surface 10; 10' of the sleeve 8; 8' and the inner surface 14; 14' of the reactor 12; 12'; 12" can suitably be kept small when treating opaque liquids in order to allow the UV light to reach as much as possible of the liquid volume passing though the liquid treatment system. At those parts of the reactor 12; 12' not having extended radius, i.e. between the sleeve outer surface 10; 10' and the first part 18; 18' of the reactor 12; 12' in the embodiment of the invention as shown in FIGS. 2b and 2c, an average of this distance can for example be between 1 and 10 mm. Due to a problem in tolerances when producing a sleeve from fused quartz (also called fused silica) the distance will often vary. Thanks to the extended radius of the reactor 12; 12' where the cleaning device 16; 16' is provided cleaning of the sleeve outer surface can be performed while still keeping a thin treatment chamber 4, i.e. a small distance between sleeve outer surface and inner surface of the reactor as described above.

FIG. 2b shows schematically a transversal cross section of a liquid treatment system 2 according to one embodiment of the invention. Most parts have been described above. In this embodiment a hollow cylindrical metal braid comprising an inner tube is used as the cleaning device 16. The reactor 12 comprises a first part 18 having a cross section being a part of a circle which is centered around the same longitudinal axis A around which the sleeve 8 also is centered. The reactor 12 comprises further a second part 20 which is connected to the first part 18 such that inner walls 14a of the first part 18 and inner walls 14b of the second part 20 together encircle the sleeve 8. The inner wall 14b of the second part 20 is provided at a greater distance from the sleeve 8 than the inner wall 14a of the first part 18. Furthermore the cleaning device 16 is provided between the second part 20 and the sleeve 8. The cleaning device 16 is compressed towards the sleeve 8 by the inner walls of the second part 20. The second part 20 can also be said to have an extended radius compared to the rest of the reactor 12. In this embodiment it can be seen that the second part 20 is connected to the first part 18 by two fasteners 31, such as screws. In another embodiment the second part 20 can be either connected to the first part 18 by other means, such as a clamp, soldering or gluing or the second part 20 and the first part 18 could instead be molded together or be extruded as one part.

FIG. 2c shows schematically some details in a transversal cross section of a liquid treatment system according to another embodiment of the invention. The UV lamp 6 is not shown here. A reactor 12' is provided around the sleeve 8'. The reactor 12' comprises a first part 18' and a second part 20'. Inner walls 14b' of the second part 20' are provided at a greater distance from the sleeve outer surface 10' than inner walls 14a' of the first part 18' of the reactor 12'. Furthermore the elongated cleaning device 16' housed within the second part 20' is not a hollow cylinder in this embodiment but comprises an elongated cleaning part 16a' from abrasive material provided closest to the outer surface 10' of the sleeve 8' and an elongated elastic part 16b' provided closest to the inner surface 14' of the reactor 12'. The cleaning part 16a' can be a metal braid or steel wool and the elastic part 16b' can be a spring, foam rubber, silicon rubber or a flexible tube.

In another embodiment of the invention the elongated cleaning device 16; 16' comprises an elongated elastic part which is both elastic and abrasive such as an elastic metal braid as described above.

Figure 5:
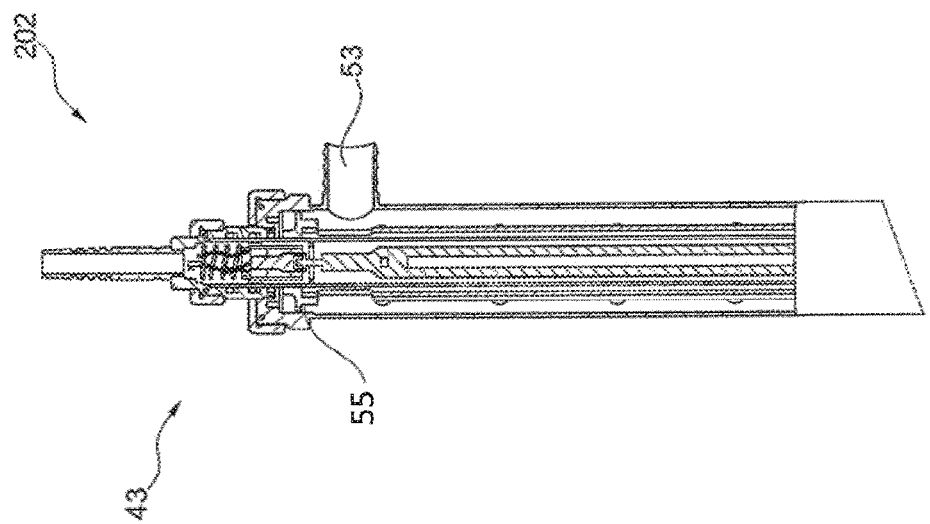
FIG. 5 is a side view, partly in cross section of the same liquid treatment system as shown in FIG. 4 but showing the opposite end of the liquid treatment system.
Figure 4:
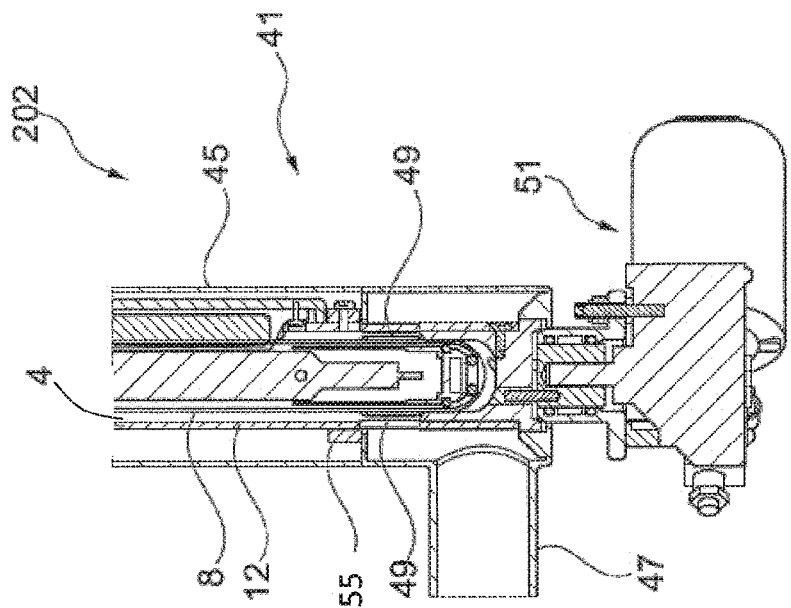
FIG. 4 is a side view, partly in cross section of a liquid treatment system according to one embodiment of the invention.

FIGS. 4-5 show a first end 41 and a second end 43 partly in cross section of a liquid treatment system 202 according to one embodiment of the invention. This liquid treatment system 201 comprises an elongated cleaning device along the sleeve as shown in FIG. 2b. The reactor 12 can be seen enclosing the sleeve 8. An outer chamber 45 is in this embodiment provided enclosing the reactor 12. Liquid can be provided into the system through a liquid inlet 47 provided in the outer chamber 45. The reactor 12 comprises openings 49 such that liquid entering the system from the liquid inlet 47 can be transferred into the treatment chamber 4 which is provided between the reactor 12 and the sleeve 8. In this embodiment it can be seen that the reactor 12 is connected to a driving mechanism 51 for rotating the reactor. However in another embodiment the sleeve could instead be rotated. An outlet 53 is provided at the second end 43 of the system 202.

In some embodiments of the invention the liquid treatment system 202 further comprises a surface bearing arrangement 55 configured for keeping the sleeve 8 and the reactor 12 axially and radially aligned while allowing at least one of the sleeve 8 and the reactor 12 to rotate around the longitudinal axis A. Such a surface bearing arrangement can be designed in different ways. Bearings can be provided at different positions in the system for keeping the sleeve and the reactor in correct position. Furthermore, if an outer chamber is provided in the system enclosing the reactor the bearings can also keep the reactor and the sleeve in position within the outer chamber. In some embodiments of the invention the reactor and the sleeve can be removed from the outer chamber for maintenance, for example change of cleaning device. In that case the bearings need to be designed for allowing removal of the reactor. This is provided in the embodiment shown in FIGS. 4-5.

Figure 8:
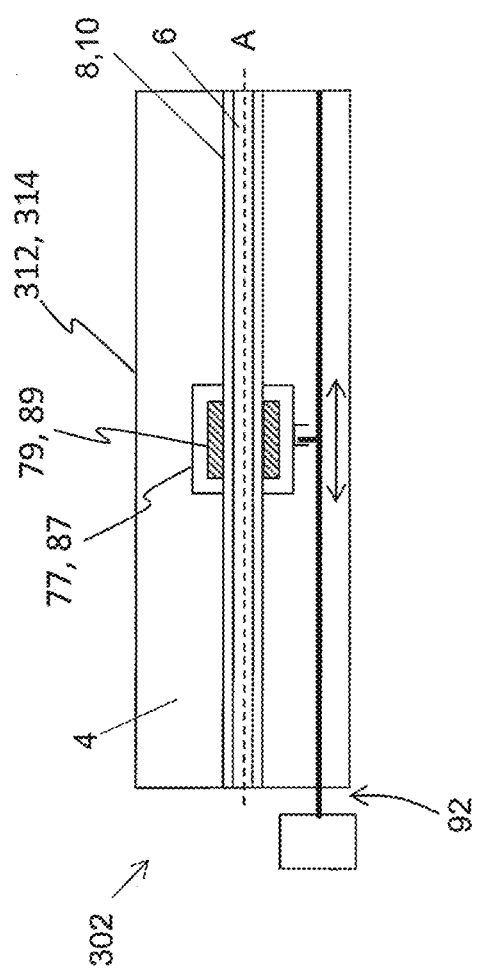
FIG. 8 shows schematically a liquid treatment system according to one embodiment of the invention in which the cleaning arrangements as shown in FIGS. 6 and 7 can be used.

FIGS. 6a-6b and FIGS. 7a-7b show different views of two different cleaning arrangements 77, 87 to be used in a liquid treatment system 302 according to another embodiment of the invention. FIG. 8 shows schematically in cross section a liquid treatment system 302 according to one embodiment of the invention in which the cleaning arrangements 77, 87 as shown in FIGS. 6 and 7 can be used.

The liquid treatment system 302 comprises at least one ultra-violet UV light treatment lamp 6 arranged within an elongated protective UV-transparent sleeve 8 provided along a central longitudinal axis A. The sleeve 8 has an outer surface 10 and an essentially circular cross-sectional shape. The liquid treatment system 302 further comprises an elongated reactor 312 configured to receive said sleeve 8, whereby an elongated liquid treatment chamber 4 for receiving liquid to be treated, is provided between an inner surface 314 of the reactor 312 and the outer surface 10 of the sleeve 8. The liquid treatment system 302 comprises further at least one cleaning arrangement 77, 87 comprising at least one cleaning device 79, 89. The cleaning arrangement 77, 87 is configured to compress said cleaning device 79, 89 towards the outer surface 10 of the sleeve 8 and to transfer the cleaning device 79, 89 over the sleeve surface 10 for cleaning the outer surface 10 of the sleeve 8. The at least one cleaning device 79, 89 comprises at least one metal braid as discussed above in relation to the previous embodiments.

The cleaning arrangement 77, 78 is configured to be moved by a driving arrangement 92 which is structured to drive the cleaning arrangement 77, 87 in the treatment chamber 4 along said sleeve 8.

In the embodiments of the invention shown in FIGS. 6 and 7 the cleaning arrangement 77, 87 comprises at least one cleaning unit 78, 88 configured to be moved by the driving arrangement 92 which is structured to drive the cleaning unit 78, 88 in said treatment chamber 4 along said sleeve 8. The cleaning unit 78, 88 is configured for holding the cleaning device 79, 89, which comprises a metal braid, such that the cleaning device is compressed towards the sleeve outer surface 10 and encircles the sleeve outer surface 10. The cleaning unit 78, 88 has a general shape of a tubular body having an inner circular cross-sectional shape adapted to the outer diameter of said sleeve 8. Furthermore the cleaning unit 78; 88 has a length extending over only a part of the length of the sleeve 8, for example a part being less than a fifth of the length of the sleeve. The cleaning unit 78; 88 is configured for being moved along the length of the sleeve and will therefor still clean the whole or essentially the whole outer surface of the sleeve.

In the embodiment shown in FIG. 6 the cleaning device 79 is threaded back and forth in the cleaning unit 78 such that an inner surface of the cleaning unit 78 which will contact the outer surface 10 of the sleeve 8 is covered by the cleaning device 79. The cleaning device can be threaded in other alternative ways. In the embodiment shown in FIG. 7 the cleaning device 89 is instead winded around the sleeve 8 within the cleaning unit 88 such that the cleaning unit 88 holds the cleaning device 89 in a wanted position along the sleeve. The cleaning device 89 can encircle the sleeve 8 at least one turn, and suitably more than one turn. The cleaning devices 79, 89 in both embodiments shown in FIGS. 6 and 7 can be resiliently biased to said outer surface 10 of the sleeve 8 by the cleaning unit 78, 88.

The cleaning device 79, 89 comprises as discussed above a metal braid. The metal braid can be elastic in itself and/or comprise an inner elastic tube. Further details of the cleaning device have already been discussed in relation to FIGS. 1a and 1b.

The invention claimed is:

1. A liquid treatment system, comprising:
   at least one ultra-violet (UV) light treatment lamp arranged within an elongated protective UV-transparent sleeve provided along a central longitudinal axis A, said elongated protective UV-transparent sleeve having an outer surface and an essentially circular cross-sectional shape;
   an elongated reactor configured to receive said elongated protective UV-transparent sleeve, whereby an elongated liquid treatment chamber for receiving liquid to be treated, is provided between an inner surface of the elongated reactor and the outer surface of the elongated protective UV-transparent sleeve; and
   at least one cleaning arrangement comprising at least one cleaning device, wherein said cleaning arrangement is configured to compress said at least one cleaning device towards the outer surface of the elongated protective UV-transparent sleeve and to transfer the at least one cleaning device over the outer surface of the elongated protective UV-transparent sleeve for cleaning the outer surface of the elongated protective UV-transparent sleeve, wherein the at least one cleaning device includes at least one metal braid, wherein the at least one metal braid is a hollow cylinder which is braided, knitted or woven from a metallic material.

2. The liquid treatment system according to claim 1, wherein the metal braid is abrasive and the metallic material is resistant to UV light and corrosion.

3. The liquid treatment system according to claim 1, wherein the metallic material is stainless steel, monel or titanium.

4. The liquid treatment system according to claim 1, wherein the at least one cleaning device further includes an elastic inner tube inside the hollow cylinder of the at least one metal braid.

5. The liquid treatment system according to claim 1, wherein the at least one cleaning device is an elongated cleaning device provided side by side with the elongated protective UV-transparent sleeve within the elongated liquid treatment chamber and along at least a part of a length of the elongated protective UV-transparent sleeve, and wherein the at least one cleaning device is compressed towards the outer surface of the elongated protective UV-transparent sleeve by the cleaning arrangement, wherein the cleaning arrangement is a part of the elongated reactor and wherein at least one of the elongated protective UV-transparent sleeve and the elongated reactor is configured to rotate around the central longitudinal axis A such that the at least one cleaning device will be touching and cleaning the outer surface of the elongated protective UV-transparent sleeve over essentially a whole circumference of the elongated protective UV-transparent sleeve.

6. The liquid treatment system according to claim 5, wherein the elongated reactor has a partly circular cross-sectional shape with at least one part having an extended radius where the at least one cleaning device is provided and wherein said at least one cleaning device is compressed towards the outer surface of the elongated protective UV-transparent sleeve by the elongated reactor.

7. The liquid treatment system according to claim 1, wherein the at least one cleaning arrangement comprises at least one cleaning unit configured to be moved by a driving arrangement which is structured to drive the at least one cleaning unit in said elongated liquid treatment chamber along said elongated protective UV-transparent sleeve, the at least one cleaning unit being configured for holding the metal braid of the cleaning device such that the metal braid is compressed towards the outer surface of the elongated protective UV-transparent sleeve.

8. The liquid treatment system according to claim 7, wherein the cleaning device encircles the elongated protective UV-transparent sleeve at least one turn and said cleaning device being resiliently biased to said outer surface of the elongated protective UV-transparent sleeve by the at least one cleaning unit.

9. The liquid treatment system according to claim 7, wherein the at least one cleaning unit has a general shape of a tubular body having an inner circular cross-sectional shape adapted to an outer diameter of said elongated protective UV-transparent sleeve and wherein said at least one cleaning unit has a length extending over only a part of a length of the elongated protective UV-transparent transparent sleeve.

10. A liquid treatment system, comprising:
    at least one ultra-violet (UV) light treatment lamp arranged within an elongated protective UV-transparent sleeve provided along a central longitudinal axis A, said elongated protective UV-transparent sleeve having an outer surface and an essentially circular cross-sectional shape;

an elongated reactor configured to receive said elongated protective UV-transparent sleeve, whereby an elongated liquid treatment chamber for receiving liquid to be treated, is provided between an inner surface of the elongated reactor and the outer surface of the elongated protective UV-transparent sleeve; and at least one cleaning arrangement comprising at least one cleaning device, wherein said cleaning arrangement is configured to compress said at least one cleaning device towards the outer surface of the elongated protective UV-transparent sleeve and to transfer the at least one cleaning device over the outer surface of the elongated protective UV-transparent sleeve for cleaning the outer surface of the elongated protective UV-transparent sleeve, wherein the at least one cleaning device includes at least one metal braid, wherein the at least one cleaning device is an elongated cleaning device provided side by side with the elongated protective UV-transparent sleeve within the elongated liquid treatment chamber and along at least a part of a length of the elongated protective UV-transparent sleeve, and wherein the at least one cleaning device is compressed towards the outer surface of the elongated protective UV-transparent sleeve by the cleaning arrangement, wherein the cleaning arrangement is a part of the elongated reactor and wherein at least one of the elongated protective UV-transparent sleeve and the elongated reactor is configured to rotate around the central longitudinal axis A such that the at least one cleaning device will be touching and cleaning the outer surface of the elongated protective UV-transparent sleeve over essentially a whole circumference of the elongated protective UV-transparent sleeve.

11. The liquid treatment system according to claim 10, wherein the at least one metal braid is a hollow cylinder which is braided, knitted or woven from a metallic material.

12. The liquid treatment system according to claim 11, wherein the metal braid is abrasive and the metallic material is resistant to UV light and corrosion.

13. The liquid treatment system according to claim 11, wherein the metallic material is stainless steel, monel or titanium.

14. The liquid treatment system according to claim 10, wherein the metal braid is a hollow cylinder and further includes an elastic inner tube.

15. The liquid treatment system according to claim 10, wherein the elongated reactor has a partly circular cross-sectional shape with at least one part having an extended radius where the at least one cleaning device is provided and wherein said at least one cleaning device is compressed towards the outer surface of the elongated protective UV-transparent sleeve by the elongated reactor.

* * * * *